no …

United States Patent [19]

Steacy

[11] Patent Number: 4,547,205
[45] Date of Patent: Oct. 15, 1985

[54] DEHYDROCYCLODIMERIZATION PROCESS

[75] Inventor: Paul C. Steacy, Des Plaines, Ill.

[73] Assignee: UOP Inc., Des Plaines, Ill.

[21] Appl. No.: 659,924

[22] Filed: Oct. 11, 1984

[51] Int. Cl.[4] ............................................. B01D 53/04
[52] U.S. Cl. ........................................... 55/25; 55/27; 55/68; 55/75; 62/18; 62/23; 585/820
[58] Field of Search .................... 55/25-27, 55/48, 58, 62, 68, 74, 75; 62/18, 23, 24; 585/655, 802, 820, 825, 826

[56] References Cited

U.S. PATENT DOCUMENTS

| | | | |
|---|---|---|---|
| 2,992,283 | 7/1961 | Eng | 260/673 |
| 3,101,261 | 8/1963 | Skarstrom | 55/58 |
| 3,208,199 | 9/1965 | Pruiss | 55/68 X |
| 3,383,838 | 5/1968 | Carson | 55/48 X |
| 3,537,978 | 11/1970 | Borst, Jr. | 208/101 |
| 3,574,089 | 4/1971 | Forbes | 208/101 |
| 3,618,331 | 11/1971 | Smith et al. | 55/68 X |
| 3,761,389 | 9/1973 | Rollman | 208/64 |
| 3,838,553 | 10/1974 | Doherty | 55/58 |
| 3,843,512 | 10/1974 | Smith et al. | 55/68 X |
| 3,843,740 | 10/1974 | Mitchell et al. | 260/673 |
| 4,077,779 | 3/1978 | Sircar et al. | 55/68 X |
| 4,102,659 | 7/1978 | Martin | 55/68 X |
| 4,171,207 | 10/1979 | Sircar | 55/26 |
| 4,180,689 | 12/1979 | Davies et al. | 585/407 |
| 4,184,943 | 1/1980 | Anderson | 585/826 X |
| 4,280,824 | 7/1981 | Lassmann et al. | 55/26 |
| 4,329,532 | 5/1982 | Conn et al. | 585/407 |
| 4,347,394 | 8/1982 | Detz et al. | 585/419 |
| 4,367,364 | 1/1983 | Kulprathipanja et al. | 585/826 |
| 4,374,022 | 2/1983 | Fuderer | 585/655 X |
| 4,381,417 | 4/1983 | Vora et al. | 585/655 |
| 4,381,418 | 4/1983 | Gewartowski et al. | 585/655 |
| 4,444,988 | 4/1984 | Capsuto et al. | 585/415 |
| 4,455,444 | 6/1984 | Kulprathipanja et al. | 585/826 |
| 4,455,445 | 6/1984 | Neuzil et al. | 585/826 X |
| 4,482,369 | 11/1984 | Carson et al. | 62/23 X |

Primary Examiner—Robert Spitzer
Attorney, Agent, or Firm—Thomas K. McBride; William H. Page, II; John F. Spears, Jr.

[57] ABSTRACT

A process is disclosed for the recovery of hydrogen and $C_6$-plus product hydrocarbons from the effluent stream of a hydrocarbon conversion reaction zone. The effluent stream is partially condensed to remove the bulk of the heavy hydrocarbons, which are sent to a fractionation zone. The remaining vapor is compressed to a substantially higher pressure. The vapor then passes into an autorefrigeration zone in which it is cooled and partially condensed by indirect heat exchange against flashed fluids. The still pressurized uncondensed compounds are transferred to a pressure swing adsorption zone, which produces a high purity hydrogen product. The initial compression therefore is used in two different high pressure separation zones in series.

12 Claims, 1 Drawing Figure

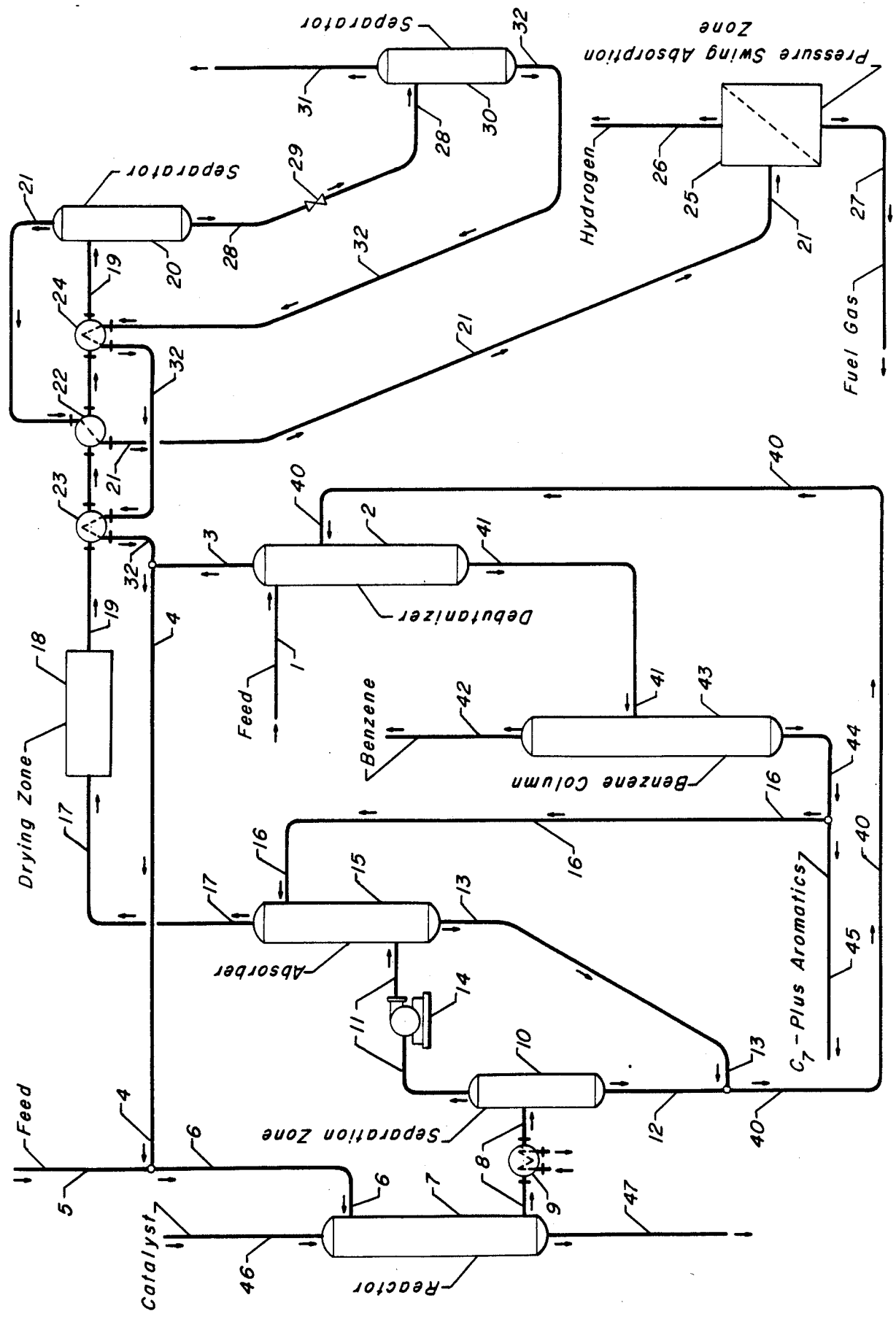

4,547,205

DEHYDROCYCLODIMERIZATION PROCESS

FIELD OF THE INVENTION

The subject process relates to a hydrocarbon conversion process. Specifically, the subject process relates to a catalytic process referred to as dehydrocyclodimerization wherein two or more molecules of a light aliphatic hydrocarbon, such as propane pr propylene, are joined together to form a product aromatic hydrocarbon. Nonaromatic hydrocarbons are also produced, especially when substantial amounts of olefins are present in the feed. The invention specifically relates to the separatory methods used to recover hydrogen and product $C_6$-plus hydrocarbons from a vapor phase reaction zone effluent stream. This separatory method also relates to techniques for recycling unconverted feed hydrocarbons to the reaction zone.

INFORMATION DISCLOSURE

There are a large number of references which describe the conversion of light aliphatic hydrocarbons to aromatic hydrocarbons. For instance, U.S. Pat. No. 2,992,283 issued to J. Eng describes the conversion of propylene to a variety of higher molecular weight hydrocarbons using a treated crystalline aluminosilicate as the catalyst. U.S. Pat. No. 4,347,394 issued to C. M. Detz et al describes the conversion of $C_5$-plus hydrocarbons to aromatics using a nonacidic zeolite supporting a platinum compound. U.S. Pat. No. 4,329,532 issued to P. J. Conn et al describes the conversion of $C_4$-minus olefins or mixtures of olefins and paraffins to aromatic hydrocarbons. The catalyst comprises a crystalline silicate having a specified composition, crystallite size range, and X-ray diffraction pattern. U.S. Pat. No. 4,444,988 issued to L. M. Capsuto et al describes a process flow for the recovery of the products of a similar process consuming a $C_2$-$C_5$ olefinic feedstock.

U.S. Pat. No. 4,180,689 issued to E. E. Davies et al describes the conversion of $C_3$-$C_8$ aliphatic hydrocarbons to aromatic hydrocarbons in a process which employs a catalyst comprising gallium supported on an aluminosilicate. U.S. Pat. No. 3,761,389 issued to L. D. Rollmann et al describes an improved process for converting $C_2$ to 400° F. hydrocarbons to aromatics over a ZSM-5 type catalyst. The improvement resides in the use of two reaction stages in series, with the first being at more severe operating conditions. U.S. Pat. No. 3,843,740 issued to T. 0. Mitchell et al also describes a process for aromatizing aliphatic feedstocks using two different catalysts in the reactor. This reference is also pertinent for the process diagram illustrating the recovery of the product aromatics by fractionation.

The separation of product hydrocarbons from a reaction zone effluent stream which also contains light hydrocarbons and possibly hydrogen is important to the successful operation of several hydrocarbon conversion processes. For instance, U.S. Pat. Nos. 3,537,978 issued to W. B. Borst, Jr. and 3,574,089 issued to J. T. Forbes describe the recovery of naphtha, hydrogen-rich recycle gas, and light hydrocarbon streams from the effluent of a catalytic reforming zone. U.S. Pat. No. 3,101,261 issued to C. W. Skarstrom illustrates a process to recover hydrogen light ends and naphtha from the effluent of a reforming reaction zone. These references are pertinent for their showing of the use of such separatory techniques as partial condensation, stripping columns, and absorption.

U.S. Pat. Nos. 4,381,417 issued to B. V. Vora et al and 4,381,418 issued to S. A. Gewartowski et al describe product recovery systems for dehydrogenation processes in which expansion of a gas stream provides fluids used as coolant media. Referring to the latter reference, the reactor effluent is cooled, dried, further cooled, and then passed into a vapor-liquid separation zone 28. The vapors from this zone are depressurized in turbine 32 to yield a cold mixed phase stream collected in separation zone 34. Liquid from this zone is flashed into the separation zone 51.

U.S. Pat. No. 3,838,553 issued to K. S. Koherty is pertinent for its description of the use of low temperatures and elevated pressures to affect the separation of vapors and for the integration of a low temperature separation zone with a pressure swing adsorptive separation zone. In FIG. 2 of this reference, the still high pressure effluent of the low temperature separation zone flows into a pressure swing adsorption zone.

BRIEF SUMMARY OF THE INVENTION

The invention is a unique method of separating the product hydrogen and $C_6$-plus hydrocarbons from the vapor phase effluent stream of a dehydrocyclodimerization process. The process is characterized by a flow scheme which features an initial compression of a vapor stream followed by integrated absorption, autorefrigeration and pressure swing adsorption zones. This allows obtaining the benefits of these different separation techniques without extensive utilities and capital costs for gas compression. A broad embodiment of the invention may be characterized as a process for the recovery of hydrogen from a vapor phase stream derived from a reactor effluent of a hydrocarbon conversion process which comprises the steps of compressing a vapor phase first process stream which comprises hydrogen and $C_1$-$C_3$ hydrocarbons; forming a vapor phase second process stream comprising hydrogen and methane and a liquid phase third process stream comprising propane by partially condensing the first process stream by cooling through indirect heat exchange against coolant media followed by vapor-liquid separation; flashing the third process stream to a substantially lower pressure and thereby forming a vapor phase fourth process stream, which comprises methane, and a liquid phase fifth process stream, which comprises propane; employing the fifth process stream as at least a portion of the coolant media used to cool the first process stream; removing the fourth and the fifth process streams from the process; and passing the second process stream into a pressure swing adsorption zone in which hydrocarbons are selectively adsorbed onto a solid adsorbent at an elevated pressure and released at a substantially lower pressure and thereby forming a hydrogen-rich effluent stream and a sixth process stream, which comprises ethane.

BRIEF DESCRIPTION OF THE DRAWING

The drawing is a simplified schematic diagram of a process which converts a propane-containing mixture fed through lines 1 and 5 into benzene removed in line 42 and $C_7$-plus aromatics removed in line 45. The effluent stream of the reactor 7 is partially condensed and separated into vapor and condensate phases. The vapor phase is compressed and processed through the absorber 15 to yield vapor which is partially condensed to yield high pressure liquid flashed into separator 30. Uncondensed high pressure vapor flows from separator 20 to a pressure swing absorbed 25. The condensate phase portion of the reactor effluent is transported into a fractionation zone comprising columns 2 and 43.

DETAILED DESCRIPTION

Processes for the conversion of light aliphatic hydrocarbons to aromatic or nonaromatic $C_6$-plus hydrocarbons have been the subject of significant development efforts as evidenced by the previously cited references. The basic utility of the process is the conversion of the low cost highly available $C_3$ and $C_4$ hydrocarbons into the more valuable aromatic hydrocarbons and hydrogen or to convert the feed hydrocarbons to higher molecular weight aliphatic products. This may be desired simply to upgrade the value of the hydrocarbons. It may also be desired to correct an overabundance of the $C_3$ and $C_4$ hydrocarbons or to fulfill a need for the aromatic hydrocarbons. The aromatic hydrocarbons are highly useful in the production of a wide range of petrochemicals, with benzene being one of the most widely used basic feed hydrocarbon chemicals. The product aromatic hydrocarbons are also useful as blending components in high octane number motor fuels.

The feed compounds to the subject process are light aliphatic hydrocarbons having from 2 to 4 carbon atoms per molecule. The feed stream may comprise a single compound or a mixture of two or more of the compounds. The preferred feed compounds are propane, propylene, the butanes, and the butylenes, with saturates being highly preferred. The feed stream to the process may also contain some $C_2$ and $C_5$ hydrocarbons. It is preferred that the concentration of $C_5$ hydrocarbons in the feed stream to the process is held to the minimum practical level. The preferred products of the process are $C_6$-plus aromatic hydrocarbons. However, dehydrocyclodimerization processes are not 100% selective and some nonaromatic $C_6$-plus hydrocarbons are produced even from saturate feeds. When processing a feed made up of propane and/or butanes, the very great majority of the $C_6$-plus product hydrocarbons will be benzene, toluene, and the various xylene isomers. A small amount of $C_9$-plus aromatics is also produced. The presence of olefins in the feed stream results in increased production of $C_6$-plus long chain hydrocarbons as products with the preferred catalyst system. Sizable olefin concentrations in the feed significantly decrease the production of aromatics.

The subject invention is directed to the recovery of the product hydrocarbons from the effluent stream of the reaction zone. Therefore, the configuration of the reaction zone and the composition of the catalyst employed within the reaction zone are not basic elements of the invention or limiting characteristics of the invention. Nevertheless, in order to provide a background to the subject invention, it is felt useful to describe the preferred reactor system. This system comprises a moving bed radial flow multi-stage reactor such as is described in U.S. Pat. Nos. 3,652,231; 3,692,496; 3,706,536; 3,785,963; 3,825,116; 3,839,196; 3,839,197; 3,854,887; 3,856,662; 3,918,930; 3,981,824; 4,094,814; 4,110,081; and 4,403,909. These patents also describe catalyst regeneration systems and various aspects of moving catalyst bed operations and equipment. This reactor system has been widely employed commercially for the reforming of naphtha fractions. Its use has also been described for the dehydrogenation of light paraffins.

The preferred moving bed reactor system employs a spherical catalyst having a diameter between about 1/64 and 1/8 inch. The catalyst preferably comprises a support material and a metallic component deposited on the support material as through impregnation or coprecipitation. The previously cited references point out that the current trend is the use of a zeolitic support material, with the catalyst referred to in the art as a ZSM-5 type zeolite being often specified as a preferred material. When properly formulated, it appears this zeolitic material by itself has significant activity for the dehydrocyclodimerization reaction. However, it is still preferred to employ a metallic component within the catalyst system to increase the activity of the catalyst. The preferred metallic component is gallium as described in the previously cited U.S. Pat. No. 4,180,689. A dehydrocyclodimerization reaction zone is preferably operated at a temperature between about 920°–1050° F. (487°–565° C.) and a pressure under 100 psig. Hydrogen-producing reactions are normally favored by lower pressures, and pressures under about 70 psig at the outlet of the reaction zone are highly preferred. Other conditions may be preferred for other reactions.

The drawing illustrates the preferred embodiment of the invention. Those skilled in the art will recognize that this process flow diagram has been simplified by the elimination of many necessary pieces of process equipment including some heat exchangers, process control systems, pumps, fractionation column overhead and reboiler systems, etc. It may also be readily discerned that the process flow presented in the drawing may be modified in many aspects without departing from the basic overall concept of the invention. For example, the heat exchangers shown in the drawing have been held to a minimum for purposes of simplicity. Those skilled in the art will recognize that the choice of heat exchange methods employed to obtain the necessary heating and cooling at various points within the process is subject to a large amount of variation as to how it is performed. In a process as complex as this, there exists many possibilities for indirect heat exchange between different process streams. Depending on the specific location and circumstance of the installation of the subject process, it may also be desired to employ heat exchange against steam, hot oil, or process streams from other processing units not shown on the drawing.

Referring now to the drawing, a first feed stream comprising an admixture of propane and butane enters a debutanizer column 2 through line 1. The $C_4$-minus hydrocarbons which enter the debutanizer 2 are concentrated into a net overhead stream carried by line 3, which is combined with a recycle stream from line 32 to form the stream flowing through line 4. This stream is admixed with a second feed stream comprising propane and butane carried by line 5 to form a charge stream which is passed into the reactor 7 via line 6. The hydrocarbons which enter the reactor 7 are therein contacted with a dehydrocyclodimerization catalyst at conditions effective to convert a significant amount of the entering paraffins to aromatic hydrocarbons, a process which also produces significant quantities of hydrogen and some lighter hydrocarbons such as methane and ethane. Preferably, the reactor 7 contains several separate stages in which the feed materials are contacted with moving beds of catalyst. When processing a saturate feed interstage heaters not shown are employed to reheat the reactants between the contacting stages. The processing of a feed having a significant olefin concentration will require the use of interstage coolers. Fresh or regenerated catalyst is passed into the top of the reactor through line 46 and the used or spent catalyst is withdrawn through line 47 for passage to regeneration facilities.

The effluent of the reactor 7 is a vapor phase stream comprising an admixture of reaction products, by-products and feed hydrocarbons. This stream will therefore contain hydrogen, ethane, methane, propane, pentane, benzene, toluene, xylenes and $C_9$ alkylbenzenes. Acyclic hexanes, heptanes and octanes may also be present depending on the feed and catalyst. This vapor phase stream is first cooled through the use of heat exchangers represented by the indirect heat exchange means 9 and is then passed via line 8 into a first vapor-liquid separation zone 10. The reaction zone effluent stream is cooled sufficiently prior to passage into zone 10 such that a very large percentage of the readily condensable $C_6$-plus hydrocarbons enter the separation zone in a liquid phase state. A liquid hydrocarbon phase comprising these $C_6$-plus hydrocarbons and dissolved lighter hydrocarbons and hydrogen is removed from the separation zone in line 12 and admixed with a stream of rich absorption zone liquid carried by line 13. This admixture of liquid phase hydrocarbons is then passed into the debutanizer column 2 through line 40. The debutanizer column separates the entering hydrocarbons into the $C_4$-minus stream removed overhead and a $C_5$-plus stream removed as a net bottoms stream through line 41. The benzene column 43 separates these $C_5$-plus hydrocarbons. A net overhead stream which is rich in benzene is removed through line 42. A net bottoms stream comprising $C_7$-plus compounds is removed through line 44. The $C_7$-plus stream is divided into the product stream removed through line 45 and a stream passed into an absorber 15 through line 16 as a lean absorption liquid. Alternatively, $C_5$ hydrocarbons may be removed as part of the overhead stream of column 2 and recycled to the reaction zone. This improves the purity of the $C_6$ fraction removed overhead from column 43.

The uncondensed portion of the reactor effluent stream is removed from the separation zone 10 through line 11. This vapor phase material is then compressed to a substantially higher pressure in the compressing means 14. Multiple stage compression with interstage cooling is normally employed to achieve the required compression. The compressed vapor stream is then passed into a lower part of the absorber 15. The vapors pass upward countercurrent to descending absorption liquid, which results in the removal of substantially all benzene from the rising vapor. Some toluene may be released from the absorption liquid, and some light hydrocarbons such as propane and butane will enter the absorption liquid. There is thereby produced a high pressure stream carried by line 17 which comprises an admixture of hydrogen, $C_1$-$C_4$ hydrocarbons and toluene.

The relatively high pressure gas stream of line 17 is passed into a drying zone 18 for the purpose of removing water which would solidify in the downstream low temperature operation. The thus dried but still high pressure gas stream is carried by line 19 through the indirect heat exchangers 23, 22, and 24 in series. The gas stream is cooled in each of these heat exchangers, with the net cooling being sufficient to cause a partial condensation of the hydrocarbons flowing through line 19. External refrigeration from a source not shown may be supplied if necessary. The fluids from line 19 are separated in the cold high pressure separator 20 into a high pressure vapor stream flowing through line 21 and a high pressure liquid stream flowing through line 28.

The high pressure vapor stream of line 21 is utilized as a coolant in the indirect heat exchange means 22 and is then passed into a pressure swing absorption zone 25. Conventional swing bed pressure differential absorption is used in this zone to separate the entering gas into a relatively high purity hydrogen stream removed through line 26 and a stream which is rich in light hydrocarbons such as methane and ethane, removed in line 27. The high pressure liquid stream flowing through line 28 is flashed through valve 29 and then passed into the cold low pressure separator 30. The flashing operation produces vapor which is mainly methane and ethane removed through line 31 and a liquid phase material comprising heavier hydrocarbons and some ethane which is removed through line 32. The liquid flowing through line 32 is employed as coolant in the indirect heat exchange means 24 and 23 and is then recycled to the reactor via lines 4 and 6. The pressure maintained in the low pressure separator is regulated to control the temperature or the composition of the cold streams separated therein. This provides a means to control the amount of ethane recycled to the reactor.

The invention may be applied to the separation of hydrogen and $C_6$-plus hydrocarbons from the effluent streams of processes other than those which produce mainly aromatic products. Some such processes are described in the previously cited references. The processing of a highly olefinic feed stream in the preferred reaction and catalyst systems will result in a product slate of over 50 mole percent aliphatics. The same process flow may be employed. The preferred embodiment of the invention is a process for the separation of the effluent stream of a dehydrocyclodimerization reaction zone which comprises the steps of partially condensing a vapor phase reaction zone effluent stream, which comprises hydrogen, methane, ethane, propane, butane, benzene, toluene, and xylenes, and separating the resultant fluids in a first vapor-liquid separation zone into a vapor phase first process stream, which comprises hydrogen and $C_1$-$C_7$ hydrocarbons, and a condensate stream which comprises benzene, toluene, and xylenes; passing the condensate stream into a fractionation zone, and recovering benzene, toluene, and xylenes from the fractionation zone; compressing the first process stream to a pressure above about 430 psig; removing benzene from the first process stream in an absorption zone; forming a vapor phase second process stream comprising hydrogen and ethane and a liquid phase third process stream comprising propane by partially condensing the first process stream through indirect heat exchange against a coolant media followed by vapor-liquid separation in a second separation zone at a pressure above about 300 psig; flashing the third process stream to a substantially lower pressure and thereby forming a vapor phase fourth process stream, which comprises methane, and a liquid phase fifth process stream, which comprises propane, with the fourth and fifth process streams being substantially cooler than the first process stream; employing the fifth process stream as at least a part of the previously referred to coolant media used to partially condense the first process stream; and passing the second process stream into a pressure swing adsorption zone in which hydrocarbons are selectively adsorbed at an elevated pressure and released at a substantially lower pressure and thereby separating the second process stream into a hydrogen-rich effluent stream and a hydrocarbon-rich sixth process stream, which comprises ethane.

It is believed that those skilled in the art of petroleum and petrochemical process design may determine proper operating conditions, vessel designs, and operating procedures for the subject process through the use of standard process design techniques after having now been appraised of the overall flow of the process. These design techniques should include a recognition that it is undesirable to pass compounds which may tend to freeze or otherwise solidify in the low temperature portion of the process. For this reason, the absorption zone is provided to remove benzene from the gas stream entering this section of the process. Likewise, the drying zone is preferably provided. The function of this drying zone is to prevent the passage of water into the low temperature equipment. The drying zone is basically required to remove the small amount of water which may be dissolved within the feed stream to the process and any water which may be present on regenerated catalyst passed into the process or released from stripping steam used to seal catalyst passageways, etc. The drying zone is preferably a swing bed desiccant-type system. It is preferred to use two beds of a suitable absorbent alumina, with facilities being provided to regenerate one of these beds while the other bed is on-stream.

The vapor-liquid separation zones employed within the process preferably comprise a suitably sized vertically oriented vessel having a demisting pad or other liquid entrainment removal means provided at the upper end. The various fractionation columns employed in the process are preferably trayed fractionation columns having sieve-type trays and being of relatively standard design. For instance, a properly designed column having 15 trays will function as the stripping column, while the first or debutanizer column may contain 22 trays and the benzene or second column may containg 55 trays. The absorption column may be a suitably sized trayed or packed column. The liquid employed as the lean absorption liquid is preferably a portion of the net bottoms stream of the second fractionation column. However, it is within the scope of the subject process that a side-cut stream removed from this or another column could be employed as the lean absorption liquid stream. Other variations in the arrangement of the fractionation columns are also possible. For instance, it is possible to replace the portion of the feed stream charged to the top of the debutanizer column with an overhead condensing system. The entire single feed stream would then flow directly into the reactor.

The vapor stream which remains after the partial condensation of the reactor effluent stream is preferably compressed from a pressure under about 80 psig to a pressure greater than 300 psig. This initial compression step is preferably sufficient to provide a high enough pressure that the remaining vapors will flow through the subsequent high pressure separation zones without any additional compression. The use of a single compression step in this manner is a central feature of the subject process flow. It is therefore further preferred that this compression step raises the gas stream from a pressure under 70 psig to a pressure in the range of 350 to 850 psig, with pressures above 430 psig being highly preferred. The pressure drops experienced by the flowing gas streams may be significant. It is preferred that the pressure drop through the process is held to a practical minimum. For instance, the vapor-liquid separation zone in which the partially condensed materials are separated (high pressure or second separation zone) should be operated at a pressure within 75 psi of the pressure at which gases are removed from the absorption zone. Preferably the pressure of the condensed hydrocarbons prior to being flashed is within 75 psig of the pressure of the gases charged to the absorption zone.

Those skilled in the art are also familiar with the design and operation of pressure swing adsorption zones. This is evidenced by the previously cited reference and U.S. Pat. Nos. 4,070,164; 4,194,890; 4,210,426; 4,229,188; and 4,238,204, which may be referred to for further description of pressure swing adsorption systems and regeneration methods. The two basic steps in the operation of these separation zones are selective adsorption from a flowing gas stream of one class of compounds at an elevated pressure followed by regeneration at a substantially lower pressure. In the subject process, hydrocarbons such as propane and butane are selectively adsorbed in the high pressure step, with only a minimal amount of hydrocarbons being adsorbed. When the adsorbent capacity of the bed is expended, it is regenerated by reducing its operating pressure sufficiently to release the hydrocarbons. A portion of the previously purified hydrogen may be circulated through the adsorbent bed during regeneration to remove released hydrocarbons which remain after depressurization. Two or more beds of adsorbent are employed, with one bed used to treat the high pressure feed gas stream while the other bed(s) is being subjected to various regeneration steps. The elevated pressure used in the adsorption step should be within the range of 350 to 850 psig with higher pressures being acceptable but not normally employed. A pressure above 450 psig is preferred. The pressure swing adsorption zone inlet pressure is preferably within about 60 psi of the pressure of the condensate which is flashed into the low pressure cold (second) separation zone. Ambient temperatures may be employed but coolers to remove the heat of adsorption can be employed. The adsorbent is normally present as a cylindrical fixed bed and may comprise such known adsorbents as natural or synthetic zeolites (molecular sieves), various aluminas, and silicas.

I claim as my invention:

1. A process for the recovery of hydrogen from a vapor phase stream derived from a reactor effluent of a hydrogen producing hydrocarbon conversion process which comprises the steps of:
   (a) compressing a vapor phase first process stream which comprises hydrogen and $C_1$ to $C_3$ hydrocarbons;
   (b) forming a vapor phase second process stream comprising hydrogen and methane and a liquid phase third process stream comprising propane by partially condensing the first process stream by cooling through indirect heat exchange against coolant media followed by vapor-liquid separation;
   (c) flashing the third process stream to a substantially lower pressure and thereby forming a vapor phase fourth process stream, which comprises methane, and a liquid phase fifth process stream, which comprises propane;

(d) employing the fifth process stream as at least a portion of the coolant media used to cool the first process stream;
(e) removing the fourth and the fifth process streams from the process; and
(f) passing the second process stream into a pressure swing adsorption zone in which hydrocarbons are selectively adsorbed onto a solid adsorbent at an elevated pressure and released at a substantially lower pressure and thereby forming a hydrogen-rich effluent stream and a sixth process stream, which comprises ethane.

2. The process of claim 1 further characterized in that the second process stream is warmed by indirect heat exchange against the first process stream.

3. The process of claim 1 further characterized in that the elevated pressure employed in the pressure swing adsorption zone is within 60 psi of the pressure of the third process stream prior to flashing.

4. A process for the recovery of hydrogen from the effluent stream of a hydrogen-producing hydrocarbon conversion process which comprises the steps of:
(a) separating a reaction zone effluent stream, which comprises hydrogen and a mixture of $C_1$–$C_7$ hydrocarbons, into a vapor phase first process stream, which comprises hydrogen and $C_1$–$C_7$ hydrocarbons, and a condensate stream in a first separation zone;
(b) passing the condensate stream into a fractionation zone in which a product of the hydrocarbon conversion process is recovered;
(c) compressing the first process stream to a pressure above 300 psig;
(d) forming a vapor phase second process stream comprising hydrogen and ethane and a liquid phase third process stream comprising propane by partially condensing the first process stream through indirect heat exchange against a coolant media followed by vapor-liquid separation in a second separation zone at a pressure above about 300 psig;
(e) flashing the third process stream to a substantially lower pressure and thereby forming a vapor phase fourth process stream, which comprises methane, and a liquid phase fifth process stream, which comprises propane, with the fourth and fifth process streams being substantially cooler than the first process stream;
(f) employing the fifth process stream as at least a part of the previously referred to coolant media used to partially condense the first process stream; and
(g) passing the second process stream into a pressure swing adsorption zone in which hydrocarbons are selectively adsorbed at an elevated pressure and released at a substantially lower pressure and thereby separating the second process stream into a hydrogen-rich effluent stream and a hydrocarbon-rich sixth process stream, which comprises ethane.

5. The process of claim 4 further characterized in that the reaction zone effluent stream comprises benzene and toluene, which are recovered as products of the hydrocarbon conversion process.

6. The process of claim 5 further characterized in that benzene is removed from the first process stream by contact with an absorption liquid prior to the partial condensation of the first process stream.

7. The process of claim 4 further characterized in that the first process stream is compressed from a pressure less than 80 psig to a pressure greater than 430 psig.

8. The process of claim 7 further characterized in that the elevated pressure employed in the pressure swing adsorption zone is within 60 psi of the pressure of the third process stream prior to flashing.

9. A process for the separation of the effluent stream of a dehydrocyclodimerization reaction zone which comprises the steps of:
(a) partially condensing a vapor phase dehydrocyclodimerization reaction zone effluent stream, which cbmprises hydrogen, methane, ethane, propane, butane, benzene, toluene, and xylenes, and separating the resultant fluids in a first vapor-liquid separation zone into a vapor phase first process stream, which comprises hydrogen and $C_1$–$C_7$ hydrocarbons, and a condensate stream which comprises benzene, toluene, and xylenes;
(b) passing the condensate stream into a fractionation zone, and recovering benzene, toluene, and xylenes from the fractionation zone;
(c) compressing the first process stream to a pressure above about 430 psig;
(d) removing benzene from the first process stream in an absorption zone;
(e) forming a vapor phase second process stream comprising hydrogen and ethane and a liquid phase third process stream comprising propane by partially condensing the first process stream through indirect heat exchange against a coolant media followed by vapor-liquid separation in a second separation zone at a pressure above about 300 psig;
(f) flashing the third process stream to a substantially lower pressure and thereby forming a vapor phase fourth process stream, which comprises methane, and a liquid phase fifth process stream, which comprises propane, with the fourth and fifth process streams being substantially cooler than the first process stream;
(g) employing the fifth process stream as at least a part of the previously referred to coolant media used to partially condense the first process stream; and
(h) passing the second process stream into a pressure swing adsorption zone in which hydrocarbons are selectively adsorbed at an elevated pressure and released at a substantially lower pressure and thereby separating the second process stream into a hydrogen-rich effluent stream and a hydrocarbon-rich sixth process stream, which comprises ethane.

10. The process of claim 9 further characterized in that at least a portion of the fifth process stream is passed into the dehydrocyclodimerization reaction zone as a recycle stream.

11. The process of claim 10 further characterized in that the condensate stream comprises propane, propane present in the condensate stream is concentrated into a net overhead stream within the fractionation zone, and in that at least a part of the net overhead stream is passed into the dehydrocyclodimerization reaction zone.

12. The process of claim 11 further characterized in that the elevated pressure employed in the pressure swing adsorption zone is within 60 psi of the pressure of the third process stream prior to flashing.

* * * * *